United States Patent [19]

Perlin

[11] 4,337,774
[45] Jul. 6, 1982

[54] MICRO SURGICAL CLIP

[75] Inventor: Alfred R. Perlin, Highland Park, Ill.

[73] Assignee: Metatech Corporation, Northbrook, Ill.

[21] Appl. No.: 187,192

[22] Filed: Sep. 15, 1980

Related U.S. Application Data

[63] Continuation-in-part of Ser. No. 915,439, Jun. 14, 1978, abandoned.

[51] Int. Cl.³ ............................................. A61B 17/12
[52] U.S. Cl. .................................... 128/325; 128/346; 24/255 SL
[58] Field of Search ..................... 128/346, 325, 334 R, 128/354; 24/255 R, 255 BS, 255 SL; 251/10

[56] References Cited

U.S. PATENT DOCUMENTS

| | | | |
|---|---|---|---|
| 2,733,716 | 2/1956 | Roberts | 128/354 X |
| 3,326,217 | 6/1967 | Kerr | 128/325 |
| 3,409,954 | 11/1968 | Schneider | 24/255 SL |
| 3,604,071 | 9/1971 | Reimels | 128/346 X |
| 3,745,616 | 7/1973 | Batts | 24/255 SL |

FOREIGN PATENT DOCUMENTS

18858 7/1914 France ................. 128/354

*Primary Examiner*—Michael H. Thaler
*Attorney, Agent, or Firm*—Leydig, Voit, Osann, Mayer & Holt, Ltd.

[57] ABSTRACT

A surgical clip for clamping of small blood vessels having arms integrally joined and terminating in a pair of flat jaws. The arms are formed of springy material and outwardly sprung. The first arm has a cam track on its outer edge which is divergently angled. A cam follower including a resilient rod is mounted cantilever-fashion on the second arm having at its end a cam follower member riding upon the cam track to bring the jaws into a desired degree of clamping force with a blood vessel. In the preferred embodiment the resilient rod is mounted in position to have a condition of maximum curvature when the cam follower is in its jaw-releasing position so that when the cam follower arm is flexed and then manually released the cam follower tends to move automatically to a clamping position. The cam track is preferably convexly curved and made up of a closely spaced series of transversely extending detent recesses.

3 Claims, 6 Drawing Figures

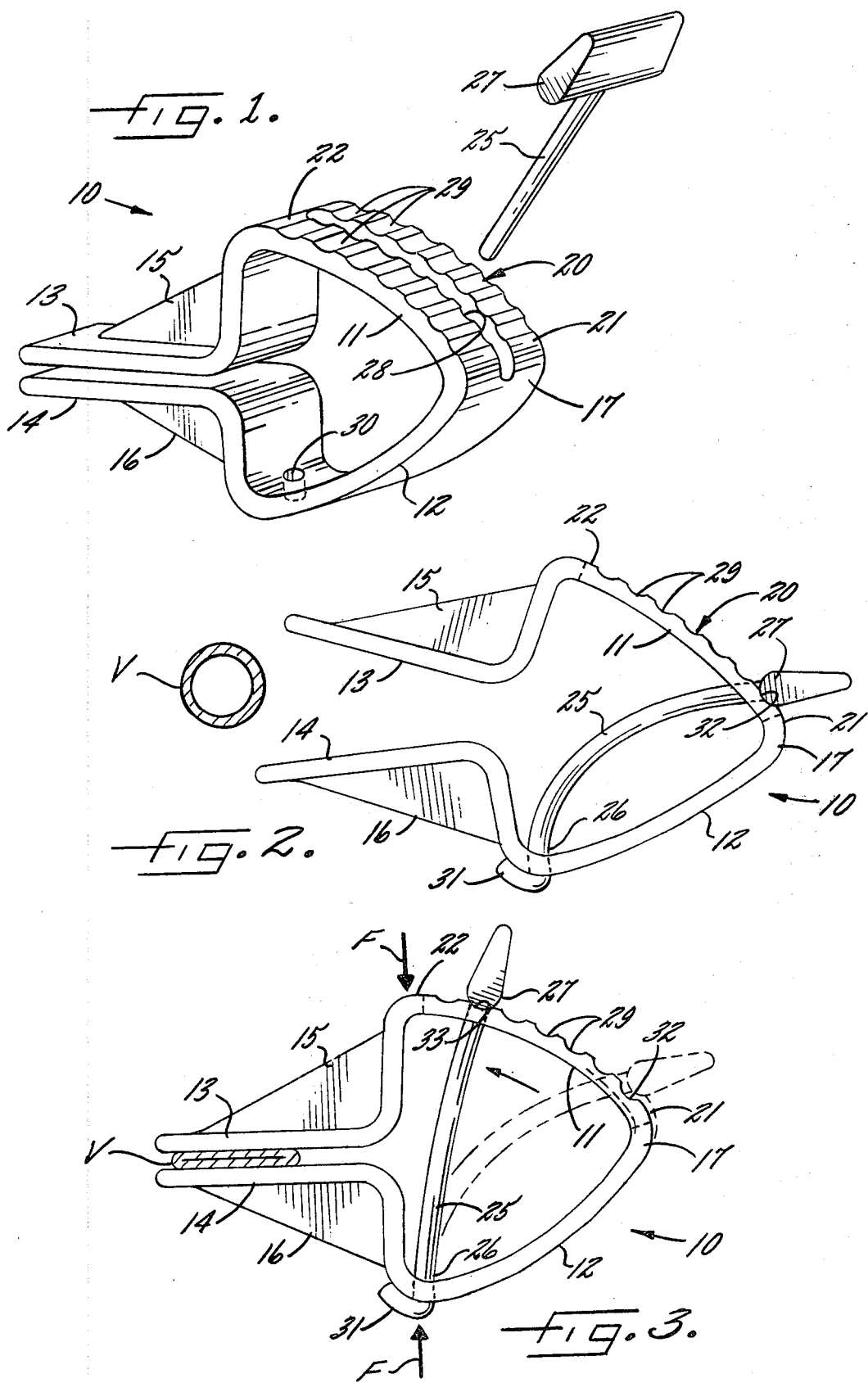

MICRO SURGICAL CLIP

This is a continuation-in-part of Application Ser. No. 915,439 filed June 14, 1978, now abandoned.

In the field of brain surgery blood vessels are numerous and relatively fragile. Conventional hemostatic clamps are constructed in a manner which requires them to be inherently large so that, when used in required number, they not only clutter and obstruct the field but they fail to provide the controllability and delicacy of clamping action which is required in this type of surgery.

The art is replete with clamps which have been developed for various specialized needs. By way of example, Roberts in U.S. Pat. No. 2,733,716 shows a clamp intended for use as an ear piercing device and which is neither intended nor suited for use in delicate surgery. Kerr in U.S. Pat. No. 3,326,217 shows a hemostatic clamp which is intended for surgical use but the structure shown is not subject to miniaturization and consists of four readily separable parts raising the distinct possibility that the device may come apart and portions thereof be lost in the wound.

Schneider U.S. Pat. No. 3,409,954 is directed to a test tube holder and Reimels U.S. Pat. No. 3,604,071 shows a plastic towel clamp; neither of these devices is intended for, nor suited to, use as a hemostatic clamp.

The French Pat. No. 18,858 of 1914 shows a clamp in the form of a tweezers which would defy miniaturization and which is obviously not suited to the present need.

It is, accordingly, an object of the invention to provide a hemostatic clamp, or clip, particularly intended for use in brain surgery, the clamp construction being particularly susceptible to a high degree of miniaturization. It is a related object to provide a hemostatic clamp in which the force applied to the blood vessel is subject to delicate and precise control on the part of the surgeon enabling positive clamping off of the blood flow, to provide a clear field, but avoiding risk that the vessel will be so tightly clamped as to be crushed or traumatized. Thus it is an object of the invention to provide a clamp which is intended for clamping of small blood vessels with a clamping force limited to forces on the order of five grams.

It is another object of the present invention, in its preferred aspect, to provide a hemostatic clamp in which the force is determined by a cam follower riding on a cam track and in which the arm which supports the cam follower is resiliently flexible. Thus upon being manually cocked into a flexed position and subsequently released the cam follower tends to return to its initial position.

More specifically it is an object to provide a hemostatic clamp in which the cam follower may be initially cocked into a flexed, jaws-open condition. When subsequently released from this position during surgery, the cam follower automatically assumes a jaws-closed clamping position in which the force exerted against the blood vessel is at a selectable safe level.

In general it is an object to provide a hemostatic clamp for use in brain surgery which is convenient and safe to operate, which can be reliably and economically constructed in a miniature size in which the largest dimension of the device is less than a centimeter permitting such clamps to be applied in large number without obstructing the operating field. It is yet another object of the invention to provide a surgical clip which is of unitary construction and in which there is no possibility that the clip may come apart while in the wound.

Other objects and advantages of the invention will become apparent upon reading the attached detailed description and upon reference to the drawings in which:

FIG. 1 is an enlarged, exploded perspective view of a surgical clip constructed in accordance with the present invention.

FIG. 2 is a side view of the clip showing it cocked to open condition in readiness for accepting a blood vessel.

FIG. 3 shows the clip of FIG. 2 following release of the cam follower and applying clamping force to the blood vessel.

Figure 4:
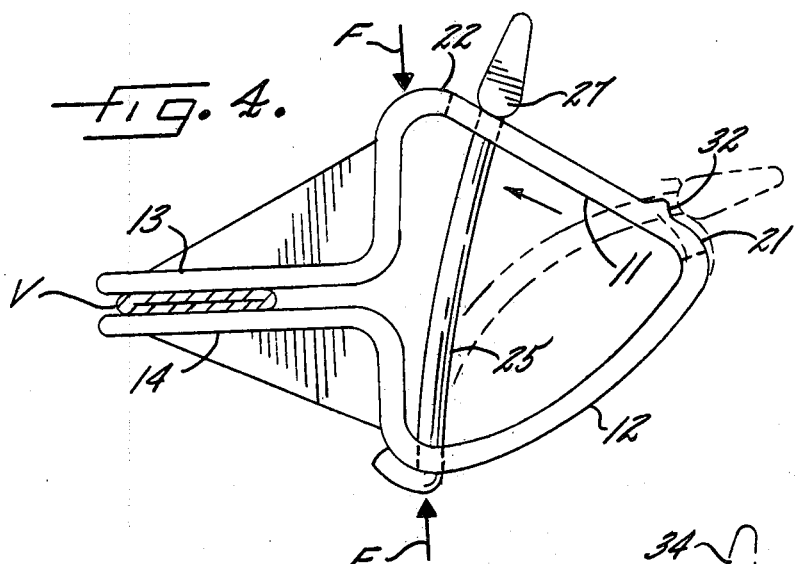
FIG. 4 shows a structure similar to that in FIGS. 1 to 3.

While the invention has been described in connection with certain preferred embodiments, it will be understood that I do not intend to be limited to the particular embodiments which have been illustrated but intend, on the contrary, to cover the various alternative and equivalent forms of the invention included within the spirit and scope of the appended claims.

Turning now to FIGS. 1 to 3 of the drawings there is shown a surgical clip 10 on a greatly enlarged scale, the clip in practice being of miniaturized construction and less than one centimeter in length. The clip includes first and second arms 11, 12 which are arranged in opposition to one another terminating in a pair of generally flat smooth jaws 13, 14 which may, if desired, be reinforced by gussets 15, 16, respectively. The arms are integrally joined at one end 17 and are formed of a springy material such as a high grade temperature resistant plastic having a relatively high elastic modulus such as that available commercially under the name of Delrin. The arms are outwardly sprung with respect to one another so that the jaws are open in the relaxed state as illustrated in FIG. 2 for interposition of a blood vessel V between them. As shown in the drawings, the arms are not only integral at the end 17 of the clip, but the two arms merge with structural continuity with one another free of any abrupt decrease in cross sectional thickness in the region of joining to strengten the joint and to enable an appreciable outward springing force to be developed.

The first arm has on its outer edge a cam track 20 which, as shown, is divergently angled with respect to the second arm 12 and which has a first, or releasing, end 21 and a second, or clamping, end 22. In carrying out the invention a cam follower arm is swingably anchored on the second arm in a fixed position and extends bridgingly to the first arm, having at its end a cam follower member which rides upon the cam track 20, the cam track being so shaped and oriented that as the cam follower is advanced progressively along the cam track from a jaw-releasing position to a jaw-clamping position the arms are cammed toward one another so that the jaws apply a desired degree of clamping force to the blood vessel. In the present instance the cam follower arm indicated at 25 is swingably anchored to the second arm 12 at a fixed position 26. The cam follower member arm carries, at its outer end, a cam follower 27 in the form of a transversely extending bar arranged in "T" formation, with the ends of the bar overlying and cooperating with the cam track 20. So as to permit the cam follower arm 25 to project through the first arm 11, the first arm is formed with a longitudinally extending slot 28 which separates the cam track 20 into two parallel portions.

Preferably and in accordance with one of the aspects of the present invention, the cam track 20 is convexly curved, as illustrated, and made up of a closely spaced series of transversely extending detent recesses 29.

The degree of clamping force applied to the blood vessel is determined by how far along the cam follower is advanced along the series of recesses 29 between the ends 21, 22 of the cam track. In utilizing the invention in a first mode it is possible to "count the clicks" as the cam follower 27 is manually pressed from the retracted position illustrated in FIG. 2 to the advanced position illustrated in FIG. 3, with the greater number of clicks signalling the distance of throw of the follower, hence a greater degree of closure and hence a greater clamping force. The clicks are not counted audibly but rather by sensing by the fingertips of the surgeon.

In accordance with one of the features of the present invention the cam follower arm is formed of a resilient rod mounted cantilever fashion on the second arm 12 so that when the cam follower is flexed and then manually released the cam follower tends to move automatically to a predetermined position on the cam track. For this purpose the cam follower arm 25 is desirably made of a short length of spring wire which may be of a non-corroding metal or, if desired, formed of resilient plastic; in the latter case the cross section of the rod would be increased appropriately to develop the required strength. The rod may be simply mounted by anchoring it in a bore 30 (see especially FIG. 1) with the rod having a projecting end 31 bent over to hold it in place and securely captive.

In carrying out the invention in its preferred form the resilient rod 25, forming the cam follower arm, is mounted in position so as to have a condition of maximum curvature when the cam follower is in its jaw-releasing position and a minimum of curvature when the cam follower is in its jaw-clamping position so that the cam follower is biased toward its jaw-clamping position. Thus as illustrated in FIG. 2 the cam follower arm has a maximum curvature when the cam follower 27 is at the jaw-releasing end 21 of the cam track, where it is latched in place in the detent recess 32. Conversely, the cam follower arm 25 has a minimum curvature when the cam follower is at the clamping end 22 of the cam track, for example, occupying a detent recess 33 as shown in FIG. 3.

The use of a cam follower arm of resilient material mounted cantilever fashion as illustrated in the figures just described permits the following novel mode of application: In advance of use the cam follower 27 is retracted or "cocked" to the jaw-releasing end 21 of the cam track accompanied by flexing of the rod 25, with the cam follower being retained in its cocked position by latching in the detent recess 32. The clip is then slipped over the bood vessel V so that the vessel is interposed between the jaws 13, 14, at which time the surgeon applies a pinching fingertip force in the direction of the arrows F-F in FIG. 3. Such pinching force moves the jaws together, at the same time releasing cam follower 27 so that the cam follower arm 25 which supports it is free to straighten under its stored force of bias, with the result that the cam follower 27 is free to travel from one end 21 of the cam track to the other end 22 where it engages the detent recess 33, as illustrated in FIG. 3. The surgeon can now release the pinching force, whereupon the cam follower 27 will assert itself to hold the clip in its clamping position.

Subsequently, when it is desired to release the clamping force, the cam follower 27 may be "clicked" or retracted by light manual pressure back to the "cocked" position illustrated in FIG. 2 accompanied by opening of the jaws.

For illustrative purposes the detent recesses 29 have been exaggerated in depth. However, it will be understood that to bring about the mode of operation discussed above the depth of the recesses, that is, the degree of detenting, should be minimized consistently with secure latching of the cam follower 27 in its cocked position.

Indeed, if desired, the detenting recesses, except for the recess 32 which serves as a latch, may be omitted as illustrated in FIG. 4 to provide greater freedom of the cam follower to move along the cam track from the first end 21 to the second end 22. In the design illustrated in FIG. 4 it is desirable for the spring in its illustrated position to be sufficiently flexed so that there is a sufficient residual bias to produce a crowding action of the cam follower 27 against the angled surface of the cam track 20 so as to keep the clip closed with a desired low level of clamping force against the blood vessel without reliance having to be placed upon detent recess 33 (FIG. 3). The operation of the slightly modified device of FIG. 4 is the same as that previously described: The cam follower 27 is retracted or cocked into the dot-dash position accompanied by flexing of the rod 25 and which is latched in detent recess 32. This opens the jaws so that the device is ready for application. Interposing a blood vessel between the jaws and applying a pinching force F releases the cam follower 27 from its latched (dot-dashed) position so that the cam follower arm undergoes a straightening motion moving the cam follower along the cam track into the vessel-clamping position illustrated in FIG. 4, where the degree of clamping force is dependent upon the strength and degree of residual flexing of the rod 25. Subsequently, to remove the clip, the cam follower is simply retracted back to its latched (dot-dashed) condition accompanied by re-opening of the jaws.

Figure 5:
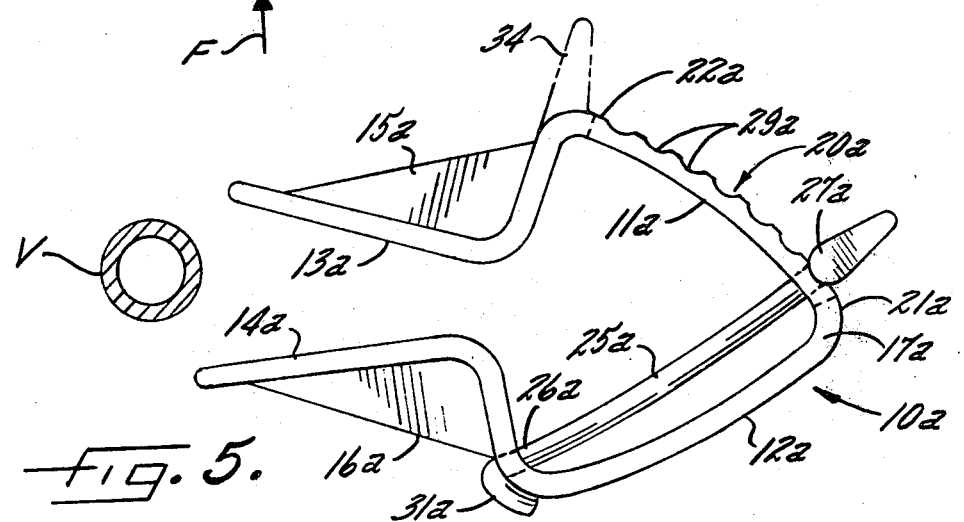
FIG. 5 is a side view of a modified form of the invention in which the cam follower arm is biased to the open rather than clamping position.
Figure 6:
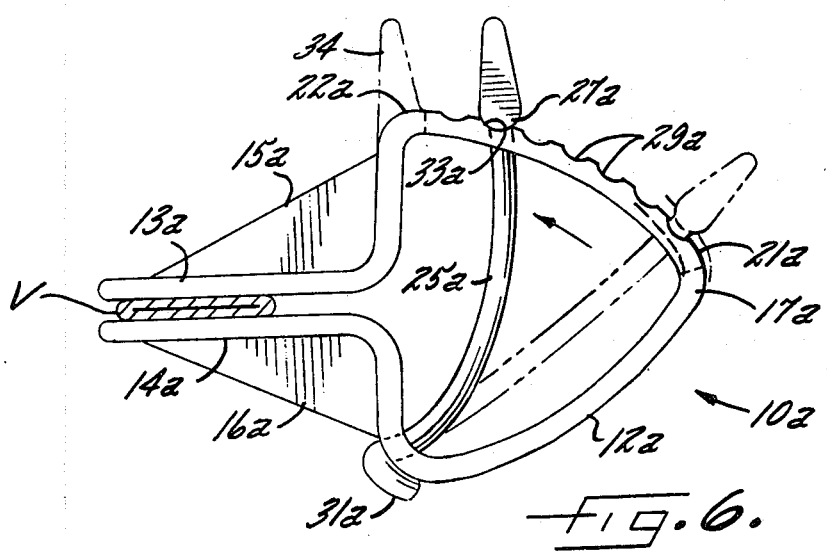
FIG. 6 shows the clip of FIG. 5 in its clamped condition.

In accordance with one of the aspects of the present invention a further mode of operation is possible and may be desired in some applications of the clip. This is brought about by a different angling of the cantilever-mounted cam follower arm as illustrated in FIGS. 5 and 6, where similar reference numerals are employed to illustrate similar elements but with addition of subscript a. In this modification of the invention the resilient rod 25, which forms the cam follower arm, is mounted, i.e., angled, in position so as to have a condition of maximum curvature when the cam follower is in its jaw-clamping position and a minimum curvature when the cam follower is in its jaw-releasing position so that the cam follower is biased toward the jaw-releasing position.

Thus comparing the structure shown in FIG. 5 with that shown in FIG. 2, both of the figures illustrating the open condition, it will be noted that the resilient rod 25a is so angled as to be in the straight or relaxed state while the rod 25 is shown in the condition of maximum curvature. This difference in cantilevered position brings about a novel difference in mode of use. There is, for example, no initial cocking necessary to establish the open condition and prior to interposing a blood vessel between the open jaws. The device as illustrated in FIG. 5 is simply slipped over the blood vessel following which the cam follower 27a is clicked along the detents 29a progressively flexing the rod 25a and closing the jaws until the blood vessel is securely but lightly clamped and the cam follower reaches a position toward the end of the cam track 22a where it engages a detent recess 33a. To facilitate applying fingertip pressure to the cam follower 27a an optional abutment 34 may be formed on the first arm 11a. Use of such abutment gives the user a ledge or pedestal for application of reaction force, permitting the cam follower to be advanced with a more convenient pinching action and providing a finer degree of control of the degree of advancement.

Subsequently, when it is desired to remove the clip from the vessel two modes of operation are possible: A momentary force may be applied transversely with respect to the clip as indicated at F in the earlier figures which produces an incremental clamping movement which is adequate, in any event, to free the cam follower 27a from the recess 33a which holds it thereby permitting the resilient rod 25a which supports the cam follower to straighten under its force of bias to its more relaxed state so that the cam follower 27a automatically restores itself to the condition illustrated in FIG. 5 accompanied by opening of the jaws to free the blood vessel.

Alternatively, the device, illustrated in clamping position in FIG. 6, may be released by simply applying manual retracting force to the cam follower 27a clicking it reversely along the cam track until the open condition illustrated in FIG. 5 is restored.

It is seen, therefore, that it is one of the features of the present invention that the cam follower arm is both resilient and mounted cantilever-fashion so that, when the cam follower arm is flexed and then manually released, the cam follower tends to move automatically to a predetermined position on the cam track. This predetermined position corresponds to closure of the jaws in the preferred embodiment illustrated in FIGS. 1–4 and to opening of the jaws in the case of the second embodiment illustrated in FIGS. 5 and 6. Which of the two modes is employed is a matter of personal choice of the surgeon. Each has its advantages.

However, it is a further feature of the construction that the automaticity provided by the flexed cam follower arm need not be used and the device may be employed in a simple manual mode which involves clicking the cam follower along the cam track progressively in one direction (from 21 to 22) to close the clip upon a blood vessel until a desired clamping force is being exerted and moving the cam follower in the opposite direction for opening of the jaws to enable the vessel to be released. If this is the mode desired by the surgeon, the cantilever mount, and the accompanying flexing of the rod, may be dispensed with and the anchored end 26 of the rod may, in effect, be hinged to the second arm for swinging movement in the plane of the clip. This can be achieved simply by employing an oversized hole at 30 (FIG. 1) to permit broadwise swinging movement of the arm about its point of anchorage.

It will be apparent from the above that the present surgical clip amply meets the objects of the invention. The structure is suited to a high degree of miniaturization and is thus capable of simultaneous clamping of numerous blood vessels in a crowded field as encountered, most notably, in brain surgery. The force applied to the blood vessel is subject to delicate and precise control and the rise of trauma by over-clamping is avoided. By employing a resiliently flexible cam follower arm, cantilever mounted, a degree of automaticity is brought about wherein the device may be cocked open prior to application and triggered for movement to closed position by the stored force of bias. Or the converse operation is possible, as described. Contrasted with other types of clamps now in use the device is unitary and selfcontained so that it is not possible to inadvertently lose a piece of it in the operating field.

Notwithstanding its numerous features and advantages the device is highly economical to construct, particularly employing quantity production techniques, as compared to the highly expensive clips now in use; indeed, the cost of the clip is so low as to permit discard after a single usage, even if made in larger size.

While the present clip, notwithstanding its small size, may be manually applied by the fingertips of the surgeon, it is one of the features of the construction that it is well suited for application by special mechanical applicators which, however, do not form a part of the present disclosure.

What I claim is:

1. A surgical clip for clamping of small blood vessels comprising first and second arms arranged in opposition to one another terminating in a pair of opposed generally flat and smooth jaws, the arms being integrally joined at one end and merging with structural continuity with one another free of any abrupt reduction in cross sectional thickness in the region of joining, the arms being formed of a springy material for movement toward and away from one another, the arms being outwardly sprung so that the jaws tend to occupy positions spaced from one another for interposition of a blood vessel between them, the first arm having along its outer edge a cam track which is divergently angled with respect to the second arm, a cam follower arm swingably anchored in a fixed position on said second arm and extending bridgingly to the first arm and having at its end a cam follower member riding upon the cam track and projecting uniformly outwardly from the first arm along the entire cam track for convenient fingertip manipulation, the cam track being so shaped and oriented that as the cam follower member is advanced progressively along the cam track between a jaw-releasing position and a jaw-clamping position the arms are cammed toward or allowed to move away from one another so that the jaws apply a desired degree of clamping force to the blood vessel, said cam track having formed thereon a closely spaced series of shallow detent recesses in the path of the cam follower member and along which the cam follower member may be manually pressed by substantially equal light manual pressure in opposite directions to adjust the clamping positions of the jaws while sensing the number of clicks as a measure of the distance traversed, the cam follower arm being formed of a resilient rod mounted cantilever-fashion on said second arm so that when the cam follower arm is flexed and then manually released the cam follower member tends to move automatically to a predetermined position on the cam track.

2. The combination as claimed in claim 1 in which the resilient rod is cantilever-mounted in angled position so as to have a condition of maximum curvature when the cam follower is in its jaw-releasing position and minimum curvature when the cam follower is in its jaw-clamping position so that the cam follower is biased toward its jaw-clamping position.

3. The combination as claimed in claim 1 in which the resilient rod is cantilever-mounted in angled position so as to have a condition of maximum curvature when the cam follower is in its jaw-clamping position and minimum curvature when the cam follower is in its jaw-releasing position so that the cam follower is biased toward its jaw-releasing position.

* * * * *